(12) United States Patent
Sato et al.

(10) Patent No.: US 8,048,866 B2
(45) Date of Patent: Nov. 1, 2011

(54) PREVENTIVE AND/OR THERAPEUTIC AGENT FOR CALCIPENIA

(75) Inventors: Tadashi Sato, Obihiro (JP); Tomokazu Nakai, Obihiro (JP); Tsutomu Aritsuka, Obihiro (JP); Tetsuo Nanbu, Obihiro (JP); Hiroo Sadoya, Obihiro (JP); Etsuo Imura, Obihiro (JP)

(73) Assignee: Nippon Beet Sugar MFG., Co., Ltd., Tokyo (JP)

( * ) Notice: Subject to any disclaimer, the term of this patent is extended or adjusted under 35 U.S.C. 154(b) by 964 days.

(21) Appl. No.: 11/573,458

(22) PCT Filed: Aug. 13, 2004

(86) PCT No.: PCT/JP2004/011944
§ 371 (c)(1),
(2), (4) Date: Feb. 9, 2007

(87) PCT Pub. No.: WO2006/016424
PCT Pub. Date: Feb. 16, 2006

(65) Prior Publication Data
US 2009/0209484 A1     Aug. 20, 2009

(51) Int. Cl.
*A61K 31/7016* (2006.01)
*A61P 3/14* (2006.01)

(52) U.S. Cl. .................................................. 514/53

(58) Field of Classification Search .................. None
See application file for complete search history.

(56) References Cited

FOREIGN PATENT DOCUMENTS

| JP | 63 269962 | 11/1988 |
|---|---|---|
| JP | 63-269962 | 11/1988 |
| JP | 1-285195 | 11/1989 |
| JP | 5-168419 | 7/1993 |
| JP | 5 168419 | 7/1993 |
| JP | 5-279377 | 10/1993 |
| JP | 11 43438 | 2/1999 |
| JP | 11-43438 | 2/1999 |
| JP | 11-155520 | 6/1999 |
| JP | 11-155564 | 6/1999 |
| JP | 2000-60541 | 2/2000 |
| JP | 2000-204042 | 7/2000 |
| JP | 2000 204042 | 7/2000 |
| JP | 2002-68970 | 3/2002 |
| JP | 2003-321371 | 11/2003 |
| JP | 3514955 | 1/2004 |
| JP | 2004-329110 | 11/2004 |
| WO | 03 090759 | 11/2003 |

OTHER PUBLICATIONS

Mitamura R. and Hara, H. and Aoyama, Y. and Chiji, H., Journal of Nutrition, Supplemental Feeding of Difructose Anhydride III Restores Calcium Absorption Impaired by Ovariectomy in Rats, (2002), vol. 132, pp. 3387-3393.*
WordNet Search 3.0 "prevent"; also availale at http://wordnetweb.princeton.edu/perl/webwn; last viewed Nov. 14, 2007.*
Shigematsu, N. et al., Biosc. Biotechnol. Biochem. "Effect of Difructose Anhydride III on Calcium Absorption in Humans", vol. 68, issue 5, pp. 1011-1016 (Jan. 2004).*
Sowers, M. F., Journal of the American Medical Association, "Changes in Bone Density with Lactation", vol. 269, pp. 3130-3135 (1993).*
Goff, J. P., The Veterinary Clinics of North America: Food Animal Practice, "Pathophysiology of calcium and phosphorous disorders", vol. 16, issue 2, pp. 319-337, vii; Jul. 2000.*
USDA, "National Organic Program, Dry Matter Demand Tables for Classes of Dairy Cattle"; also available at www.ams.usda.gov/nop or http://www.ams.usda.gov/AMSv1.0/getfile?dDocName=STELPRDC5082662&acct=noprulemaking; published Mar. 2010.*
Tadashi Sato, et al. "Effect of Ruminal Bacteria on Degradability of Difructose Anhydride III", Animal Science Journal, vol. 77, No. 3, Aug. 2006, pp. 395-399 (with English abstract).
Tadashi Sato, et al. "Effect of Difructose Anhydride III on Hypocalcemia in Dairy Cows After Calving", Animal Science Journal, vol. 78, No. 1, Feb. 2007, pp. 37-43 (with English abstract).
Tadashi Sato, et al., The Lecture Abstract Book of the 104th General Meeting of Japanese Society of Animal Science, Mar. 2005, (with English abstract).
Takuya Suzuki, et al. "Effects of Difructose Anhydride III on Calcium Absorption in Small and Large Intestines of Rats", Biosci. Biotechnol. Biochem., vol. 62, No. 5, 1998, pp. 837-841.
Katsuichi Saito, et al. "Effects of DFA IV in Rats: Calcium Absorption and Metabolism of DFA IV by Intestinal Microorganisms". Biosci. Biotechnol. Biochem., vol. 63, No. 4, 1999, pp. 655-661.
Hitoshi Mineo, et al. "Various Indigestible Saccharides Enhance Net Calcium Transport From the Epithelium of the Small and Large Intestine of Rats in Vitro", The Journal of Nutrition, vol. 131, No. 12, 2001, pp. 3243-3246.
Christopher S. Kovacs, "Calcium and Bone Metabolism in Pregnancy and Lactation", The Journal of Clinical Endocrinology and Metabolism, vol. 86, No. 6, XP002571142, Jun. 2001, pp. 2344-2348.

* cited by examiner

*Primary Examiner* — Shaojia Anna Jiang
*Assistant Examiner* — Bahar Schmidtmann
(74) *Attorney, Agent, or Firm* — Oblon, Spivak, McClelland, Maier & Neustadt, L.L.P.

(57) ABSTRACT

The invention is to develop an agent having at least one of anticalcipenic, antiedemic and diuretic activities for humans or animals and to inhibit the postpartum drop of the calcium concentration in blood, thereby maintaining the health of the mother body and smoothing nursing and lactation.
In the invention, difructose anhydride (DFA) being a disaccharide made of two molecules of fructose coupled together is administered. In particular, for inhibiting the postpartum drop of the calcium concentration in blood, DFA III and/or DFA IV is administered before childbirth delivery (in a cow, before an expected date of calving). The joint use of a calcium agent or vitamin D is possible as required.

5 Claims, 4 Drawing Sheets

PREVENTIVE AND/OR THERAPEUTIC AGENT FOR CALCIPENIA

CROSS-REFERENCE TO RELATED APPLICATIONS

This application is a 371 of PCT/JP2004/011944 filed Aug. 13, 2004.

TECHNICAL FIELD TO WHICH THE INVENTION BELONGS

The present invention relates to a preventive and/or therapeutic agent for calcipenia in blood or milk, comprising difructose anhydride (DFA, hereinafter sometimes referred to as DFA) as an active ingredient.

More specifically, the invention relates to a preventive and/or therapeutic agent for calcipenia in blood or milk, comprising as an active ingredient one or more selected from difructose anhydride I (hereinafter sometimes referred to as DFA I), difructose anhydride II (hereinafter sometimes referred to as DFA II), difructose anhydride III (hereinafter sometimes referred to as DFA III), difructose anhydride IV (hereinafter sometimes referred to as DFA IV) and difructose anhydride V (hereinafter sometimes referred to as DFA V).

BACKGROUND ART

Even though eating habits have been improved especially a calcium intake of Japanese people is less than a nutritional requirement, and the improvement in its point has been in demand. However, in average eating habits of Japanese people, it is actually quite difficult to ingest a satisfactory amount of calcium.

Calcium has physiological functions of maintenance and adjustment of membranes, control of contraction secretion or excitation process, support of the stomach and the like, and it is one of Minerals indispensable in the human body, and quite important as is generally known. For an woman after child-birth delivery (after confinement), the calcium concentration in blood is decreased, and a tendency of further decreasing a calcium concentration in milk or a lactation amount is observed in a woman during nursing. In addition to the decrease in calcium concentration of mother's milk hypocalcemia or the like occurs in the mother body itself to injure the health of the mother body. To cope with these problems a calcium agent or vitamin D has been administered, but satisfactory results have not yet been provided.

In mammals such as a cow, the problems on calcium are similar to the foregoing problems in humans. Calcium to be fed to milk of a cow being a mammal is calcium in blood, and migrates from calcium in a feed or from body tissues such as bones. The calcium concentration in blood of a cow which is typical of mammals is usually from 9 to 11 mg/dl. When calcium is supplied in excess, absorption from intestines is decreased, and an excretion amount in feces and urine is increased. Consequently, although calcium in milk is influenced by the type of the cow or milk ingredients, it is maintained approximately in a prescribed amount.

In a cow, the calcium concentration in blood is decreased at a perinatal period before and after calving to show a pathogenic state of hypocalcemia. In hypocalcemia, the calcium concentration in blood is less than 7 mg/dl. When it is less than 5 mg/dl, ananastasia occurs, and a cow is dead in a serious case. It is called milk fever, and approximately 6% of cows are attacked by this disease in the U. S. It is liable to be complicated by mastitis (coliform), displaced abomasum, retained placenta and a metabolic disease such as ketosis. Further, subclinical hypocalcemia which does not lead to occurrence of clinical symptoms takes place in 66% of multiparous cows, and cows immediately after calving are led to inappetence and are susceptible to diseases such as ketosis, retained placenta, displaced abomasum and mastitis. When hypocalcemia continues for a long period of time, the calcium concentration of milk itself might be decreased.

In the cow, the calcium balance is drastically changed from calving by the start-up of lactation. That is, a large amount of calcium is secreted in foremilk by the start-up of lactation, whereas the calcium concentration in blood is decreased. When it is notably decreased, the cow is seized with ananastasia.

As a method of improving hypocalcemia of a cow, application of vitamin D or intravenous administration of a calcium agent to a cow with milk fever has been generally conducted. However, cases in which recovery or maintenance of the calcium concentration in blood is difficult have been known. Lactation ability has been currently increased by genetic modification. Thus, a lactation yield after calving is high. These matters lead to an increase in number of cows with hypocalcemia, induce serious conditions such as ananastasia, and give an adverse effect. It has been required to conquer the calcipenia in cows.

As a management of preventing calcipenia, it has been recommended to restrict calcium and phosphorus in a feed at a dry period (a period without milking from the stop of milking at one lactation period to the date of next delivery). However, it is really impossible to prepare a feed whose calcium concentration is as low as less than 50 g per day. Accordingly, for those skilled in the art, it is now impossible to prevent calcipenia by applying this management to the actual dairy farming.

Further, it is well known that diuretic activity is important for maintaining the health or alleviating diseases in humans. This point is also the same with animals. For example, the diuretic effect is quire important for maintaining the health and alleviating diseases in mammals (ruminants) such as a cow. Specially in a cow before and after calving, udder edema occurs. In a serious case, the nipple is liable to injure and mastitis tends to concur. The mammary suspensory ligament becomes weak, and milking is difficult due to pendulous udder. For therapy of the udder edema the improvement in a control method such as exercise or massage therapy with a diuretic agents surgical operation and the like have been known. However, satisfactory effects have not yet been brought forth.

Meanwhile, as difructose anhydride (DFA) which is an oligosaccharide made of two molecules of fructose coupled together difructose anhydride I (DFA I), difructose anhydride II (DFA II) difructose anhydride III (DFA III), difructose anhydride IV (DFA IV) and difructose anhydride V (DFA V) have been known, and structural formulas thereof are as follows.

DFA I

-continued

DFA II

DFA III

DFA IV

DFA V

Regarding DFA III and DFA IV, a calcium absorption accelerating composition containing DFA III as an active ingredient and a calcium absorption accelerating composition containing DFA IV as an active ingredient have been already disclosed respectively (for example, Patent Document 1 and Patent Document 2). However, the documents do not describe that these compositions are effective for prevention or therapy of calcipenia or edema of mammals. In particular, physiological activity of DFA on ruminants having four stomachs, especially cows has been entirely unknown. Needless to say, it is not indicated at all that DFA is not degraded in these stomachs and is effective for prevention and/or therapy of calcipenia on calcium in blood or calcium in milk and edema and for diuresis.

Moreover, it is entirely unknown that hypocalcemia after delivery is prevented and/or treated by administering DFA before delivery. Thus this is quite a new knowledge to humans and other mammals.
Patent Document 1
Gazette of Japanese Patent No. 3514955
Patent Document 2
Gazette of JP-A-2000-204042

Problems that the Invention is to Solve

In the mother body after childbirth delivery (after confinement), the calcium concentration in blood is indeed decreased which is liable to affect the health. With nursing, its influence is more increased, and given to not only the mother body but also a child. This has been highlighted in the present-day society with a strong trend of rapid drop in birthrate in particular.

Such an adverse effect on the health owing to the decrease in calcium concentration is common to mammals. For example, in a cow, the calcium concentration in blood is already decreased immediately after calving. The more it is decreased, the more the vitality and appetite are decreased and the recovery tends to be retarded. When this state is further progressed, ananastasia occurs. With nursing this trend is more increased, with the result that the milk yield of a cow is decreased and life as a cow is shortened.

The diuretic activity is important for maintaining the health and alleviating diseases, and activity of decreasing (preventing) edema is important. The development of an excellent system having these activities has been also demanded at the same time. These matters are applied to not only humans but also mammals and other animals.

Under such technical circumstances, the invention has been made to inhibit the decrease in calcium concentration in blood of the mother body before and after childbirth delivery, especially after childbirth delivery (after confinement) and to effectively perform diuresis and inhibition of edema in humans and other animals.

Means for Solving the Problems

The invention has been made to achieve the foregoing objects. In view of the special objects the invention has been established from the standpoint that it is necessary to reconsider the animal experiment itself which is conducted instead of a clinical test with actual humans. The present inventors have thus focused on animals used in animal tests. Mammals such as mice and rats are ordinarily used as test animals. However, these are smaller in size than humans. The purpose of the invention is to inhibit the decrease in calcium concentration in blood of the mother body after childbirth delivery, and the invention is deeply related with the mother milk. Accordingly, the present inventors have decided to use cows as a test animal.

Cows are very large mammals in comparison to mice or rats, and a mechanism of cowls milk is quite common to that of mother milk of humans in many points. Accordingly, it can be said that data obtained on cows is by far closer to data of humans than data obtained on mice or rats and reliability thereof is also high. However, unlike mice or rats, the cows have serious problems that management is difficult a test period is quite long and a cost is high. However, the invention has succeeded in animal tests using cows upon overcoming these points, which is one of the great characteristic features of the invention. Of course, in case of cows, not humans, the obtained data can directly be used, and the data of cows can appropriately be used in other mammals.

The present inventors have screened various substances that inhibit the decrease in calcium concentration in blood using cows, and have consequently focused on DFA. The inventors have conducted assiduous investigations from various aspects, and have then found for the first time that DFA is not degraded in cattle having a special digestive system with four stomachs, unlike ordinary mammals, in spite of the complex unique stomach structure. They have further conducted investigations on the basis of this new, useful knowledge. As a result, they have found for the first time that DFA has quite useful activities of accelerating calcium absorption and increasing the calcium concentration in blood to increase the calcium concentration in milk and improve hypocalcemia. It has been also confirmed that these activities are surely exhibited and reproducibility is provided.

Generally the calcium concentration in blood is decreased in cows after calving in particular, with the result that they are susceptible to various diseases ad a risk of decreasing milk yield is high. When the parity is increased, the calcium concentration is thereby decreased, and milk yield is decreased all the more. Thus, resolution of problems peculiar to cattle, especially cows has been in demand. The invention has successfully resolved the problems peculiar to cattle. Administration of DFA to cattle, especially, perinatal cows before and after calving according to the invention is therefore quite effective.

It is further noteworthy that the most effective timing of administrating DFA has been also studied in the invention. Specifically, when the calcium concentration in blood has to be maintained or increased, DFA is usually administered at that time. According to this technical common knowledge, DFA III has been supplied to a cow after confinement for inhibition of the decrease in calcium concentration in blood after calving which is one of objects in the invention, and it has then been found that this is effective for inhibiting the decrease in calcium concentration in blood. However, the inventors have decided to further develop an effective system without being satisfied with this finding. As a result of assiduous investigations, they have succeeded in the development of a more excellent, desired new system upon reversing the way of thinking.

That is, as a result of assiduous investigations from various aspects, as stated above, the inventors have made studies from the standpoint that the method and timing of supplying DFA III are important. However, the studies have not resulted in establishing a more effective system. The inventors have then deeply felt it necessary to reverse the way of thinking. They have daringly practiced a system for inhibiting the decrease in calcium concentration after calving, not after calving according to the technical common knowledge, but before calving by which the effect is not predicted nor expected at all upon reversing the way of thinking rather than upon changing the way of thinking.

Consequently, a new knowledge has been obtained quite unexpectedly that the calcium concentration in blood is more increased by supplying DFA III at a dry period "before calving" than by supplying it "after calving", and this new knowledge greatly exceeds the technical common knowledge and the technical level. The studies have been further continued, and the following new facts have then been found for the first time.

(1) When DFA III is supplied at a dry period, the calcium concentration in blood immediately after calving is more increased than in cows without supplying it.

(2) When DFA III is supplied at a dry period, the calcium concentration in blood immediately after calving is not influenced by a decrease in calcium concentration owing to aging.

(3) Unless DFA III is supplied at a dry period, the calcium concentration in blood immediately after calving is decreased as calving is increased, and a decrease amount in one calving is presumed to be 0.6 mg/dl.

(4) When DFA III is supplied at a dry period, the calcium concentration in blood is quickly returned to a normal value, unlike a cow without supply thereof which tends to be slowly returned to a normal value owing to aging.

(5) The effect of increasing the calcium concentration in blood by supplying DFA III is greater at a dry period than immediately after calving.

The invention has been completed as a result of further studies on the basis of the foregoing profitable new findings. One of the basic technical ideas is that the decrease in calcium concentration in blood after birth (after delivery) is inhibited by administrating DFA III and/or DFA IV before birth (before delivery). Further, in the invention, it has been found for the first time that not only the administration of DFA III and/or DFA IV but also the inhibition of the decrease in calcium concentration in milk at respective periods is effective for prevention and/or therapy of calcipenia which widely includes the inhibition of the decrease in calcium concentration in blood at respective periods including a period before birth. In addition, such a profitable new knowledge has been obtained that unexpectedly, DFA III and DFA IV have excellent diuretic activity and are effective or prevention and/or therapy of edema such as udder edema.

It has been further newly found that these useful effects are enhanced with calcium and/or vitamin D.

The invention has been made on the basis of these useful new findings, and the anticalcipenic, diuretic and antiedemic activities provided by DFA III and DFA IV have been discovered for the first time. In addition the invention is characteristic in that these activities have been confirmed using cattle, especially cows closer to humans, not mice or rats, as test animals.

Of course, when cattle is used in the invention, the data thereof can directly be used. When other animals are used, these new physiological activities can be confirmed as in cattle.

BRIEF DESCRIPTION OF THE DRAWINGS

FIG. 4 shows a change in calcium concentration in blood after calving. The blood sampling time after calving is a time that lapses from the blood sampling immediately after calving. In examples "Yes-Present calving" indicates an average value of cows (8 cows) to which DFA III is supplied at a dry period and which experience present calving. "Yes-Previous calving" indicates data in the previous calving of "Yes-Present calving" cows which data is data of cows to which DFA III is not supplied at a dry period in the previous calving. "No-Present calving" indicates an average of cows (7 cows) to which DFA III is not supplied at a dry period and which experience present calving "No-Previous calving" indicates data of "No-Present calving" cows which is data of cows to which DFA III is not supplied at a dry period. "No-Average of all cows" indicates an average value of all data of cows to which DFA III is not supplied at a dry period (38 cows).

The invention is described in detail below.

The invention is as follows.

1. A preventive and/or therapeutic agent of at least one of calcipenia, edema and reduction in urine amount for humans or animals, the agent comprising difructose anhydride (DFA) as an active ingredient.

2. The preventive and/or therapeutic agent of at least one of calcipenia, edema and reduction in urine amount for humans or animals as recited in 1 wherein the difructose anhydride (DFA) comprises one or more selected from difructose anhydride I (DFA I), difructose anhydride II (DFA II), difructose anhydride III (DFA III), difructose anhydride IV (DFA IV) and difructose anhydride V (DFA V).

3. A preventive and/or therapeutic agent of at least one of calcipenia, edema and reduction in urine amount for humans or animals the agent comprising difructose anhydride III (DFA III) and/or difructose anhydride IV (DFA IV) as an active ingredient.

4. The agent as recited in any one of 1 to 3, wherein calcium and/or vitamin D is further jointly used.

5. The agent as recited in any one of 1 to 4, wherein the animals are at least one selected from ruminants, other mammals, pets and birds.

6. The agent as recited in any one of 1 to 5 wherein calcipenia is a decrease in calcium concentration in blood and/or in milk.

7. The agent as recited in any one of 1 to 6, wherein the animals are cows before calving or after calving.

8. A preventive and/or therapeutic agent of hypocalcemia for administration to humans or animals before delivery, the agent comprising DFA III and/or DFA IV as an active ingredient.

9. A preventive and/or therapeutic method of at least one of calcipenia, edema and reduction in urine amount, which comprises administering the agent as recited in any one of 1 to 8 orally and/or parenterally.

10. The method as recited in 9, wherein the administration is conducted before calving and/or after calving.

11. The method as recited in 9 or 10, wherein the oral administration is conducted before calving to inhibit the decrease in calcium concentration in blood after calving.

12. A method of inhibiting a decrease in calcium concentration in blood after calving, which comprises administering DFA III and/or DFA IV to humans or animals before calving.

13. The method as recited in 12, wherein calcium and/or vitamin D is further jointly used.

14. The method as recited in 12 or 13, wherein the administration is started 2 weeks, preferably 3 weeks before an expected date of calving.

15. A method of inhibiting a decrease in calcium concentration in blood after calving, which comprises administering DFA III and/or DFA IV to a cow at a dry period.

16. The method as recited in 15, wherein DFA III or DFA IV is orally administered at a dose of from 1 to 200 g, preferably from 5 to 100 g, more preferably from 8 to 80 g, especially preferably from 10 to 70 g per day for one cow.

17. Foods and drinks or feeds which comprise DFA III and/or DFA IV and have at least one of anticalcipenic, antiedemic and diuretic activities and which are indicated to be used in calcipenia and for improvement of edema or diuresis.

18. Foods and drinks or feeds which comprise DFA III and/or DFA IV and have activity of inhibiting a decrease in calcium concentration in blood after calving and which are indicated to be used before calving for inhibiting the decrease in calcium concentration in blood after calving.

19. The foods and drinks or feeds as recited in 18, which are used for humans or animals.

20. The feeds as recited in 19, wherein the animals are at least one selected from cattle, goats, sheep, buffaloes, camels, horses, pigs and pets.

21. The feeds as recited in 20, wherein the cattle is a cow.

In the invention, DFA (DFA I, DFA II, DFA III, DFA IV and/or DFA V), especially DFA III and/or DFA IV is used as an active ingredient. Calcium and/or vitamin P is further jointly used as required DFA III (difructose anhydride III) used in the invention as an active ingredient is a disaccharide made of two molecules of fructose coupled together at 1,2' and 2,3'(di-D-fructfuranose-1,2;2,3' dianhydride). DFA III has been lately industrially produced. Further, DFA IV (difructose anhydride-IV) used as an active ingredient is a disaccharide made of two molecules of fructose coupled together at 2,6':6,2' (di-D-fructfuranose-2,6:6.2' dianhydride).

As the active ingredient, at least one of a purified product, a coarsely purified product, an intermediate product formed during production and a waste liquor of DFA I, DFA II, DFA III, DFA IV and/or DFA V, and treated products thereof (at least one of a concentrated product, a paste, a dried product, a diluted product, a suspension and an emulsion) is included. Moreover, commercial products are also available as required.

According to the invention, foods and drinks for animals, namely, feeds or feed compositions (including drinks) and/or animal agents (nutrient supplements, oral administration agents and the like) are prepared using the foregoing active ingredient. At this time, DFA I, DFA II, DFA III, DFA IV and/or DFA V are/is supplied, as a feed or a drink, in an amount of from 10 mg to 1,000 mg, preferably from 100 mg to 300 mg/day/kg of weight of animals, and as a nutrient supplement or an oral administration agent, in an amount of from 10 mg to 1,000 mg, preferably from 100 mg to 300 mg/kg of weight of animals for one administration, from once to three times. These supply amounts are not limited to the foregoing ranges, and may be deviated therefrom.

In case of using DFA I, DFA II, DFA III, DFA IV and/or DFA V in the invention as the active ingredient, the ratio thereof to calcium in a feed or a pharmaceutical composition is from 0.1 to 2 or more, preferably 0.5 to 1.5 in terms of a weight ratio when supplying the same as a feed or a drink, and is from 0.2 to 3 or more preferably from 1 to 2 in terms of a weight ratio as a nutrient supplement and an oral administration agent. However, when the supply is conducted over a long period of time or an effect of improvement in diseases is expected, the ratio may be deviated from the foregoing range.

The dose of the active ingredient, when administered to humans, can be the same as in the administration before confinement, which will be later described. In the case except the inhibition of the decrease in calcium concentration in blood, the method and the dose can properly be defined also in the foregoing manner.

In the invention, the animals are animals except humans, generally meaning animals which humans breed. The animals are ruminants as well as mammals and birds which are bred or proliferated for specific purposes or as pets Examples thereof include pigs, horses, dogs, cats, rabbits, hamsters, guinea pigs, kangaroos, monkeys, chickens, ducks, quails, ostriches, turkeys, pets, and animals and birds which are bred in zoos or the like. Ruminants include a wide variety of domestic animals such as cattle, goats, sheep, camels and buffaloes, and wild ruminants. Ruminants have a unique digestive system with the rumen, which is different from that of ordinary mammals, and they are peculiar animals to which the technical common knowledge in ordinary mammals cannot be applied directly.

The invention is effective for prevention and/or therapy of calcipenia of humans and domestic animals including ruminants Examples of calcipenia include inhibition of calcium absorption, decrease in calcium concentration in blood, decrease in calcium concentration in milk and the like. Since the active ingredient of the invention has the excellent diuretic activity, it is also effective for prevention and/or therapy of udder edema and the like.

Thus, the invention is effective for enhancing calcium in milk of lactation animals or improving hypocalcemia and is capable of therapy or prevention of the decrease in calcium concentration in blood. Accordingly, therapy or prevention of diseases caused by hypocalcemia is attained, and therapy or prevention of the decrease in calcium concentration in blood caused by confinement is possible. Owing to the diuretic activity therapy or prevention of udder edema is also possible The invention is quite effective for humans and especially for lactation ruminants such as cows.

With respect to the inhibition of the decrease in calcium concentration by the active ingredient of the invention, the present inventors have conducted further investigations, and have consequently found the quite unexpected effect, for the first time, that although the object of the invention is to inhibit the decrease in calcium concentration in blood after confinement, the very object can be attained by administering DFA III not after confinement but before confinement. A novel invention has been completed that the decrease in calcium concentration in blood after confinement is inhibited by administration before confinement.

The invention is described in detail below using, as a typical example, DFA III as an active ingredient.

DFA III may be administered before confinement (before birth). It is administered preferably one week, more preferably from two to five weeks before an expected date of confinement (expected date of birth). Administration is usually started three weeks (approximately 20 days) before confinement. Since the timing of starting administration is based on an expected date of confinement, it is unavoidable to somewhat change the timing. The foregoing timing is not limited as required, and any timing is available so long as it is before confinement. According to a method of increasing a dose or the like, a timing which is closer to an expected date of confinement than one week before an expected date of confinement is also available.

The dose of DFA III is from 0.05 to 10 g, preferably from 0.1 to 5 g, more preferably from 0.2 to 7 g per day for a pregnant woman in the oral administration. For example, it is usually 0.5 g. The administration may be conducted once at the total dose or twice or three times in divided portions. The administration is, in principle, continuously practiced every day. It may be practiced at intervals such as every other day.

The dose of DFA III is not particularly limited to the foregoing range. When it is ingested over a long period of time for preservation of the health or for maintenance of the health, the dose may be lower than the foregoing range. Since the active ingredient does not involve any problem in safety, it may be used at a higher dose than the foregoing range. Actually, as a result of an acute toxicity test for 10 days using mice, no death example was observed even by oral administration at a dose of 1,000 mg/kg.

The foregoing embodiment of administering DFA III is also applied to cows. It is effective to administer DFA III at a dry period. The specific administration timing is the same as in the foregoing case. The dose of DFA III is higher than in humans. It is from 1 to 200 g, preferably from 5 to 100 go more preferably from 8 to 80 g, especially preferably from 10 to 70 g per day for one cow. In Examples, 50 g thereof was administered.

DFA III may be administered either directly or by adding it to drinking water, foods or feeds in situ to form preparations when in use. It is also possible to administer DFA III as a supplement or to supply foods and drinks or feeds which have been produced by adding DFA III in advance. DFA III may be formulated into medicaments.

That is, in the invention, the active ingredient (its treated product) can properly be used in foods and drinks as such or jointly used with other foods or food ingredients in a usual manner. The composition using the active ingredient according to the invention may be in the form of a solid (powder, granules or the like), a paste, a liquid or a suspension. It may be formulated into healthy drinks using a sweetener, a sour agent, a vitamin agent and other various ingredients which are ordinarily used in production of drinks. This is also the same with feeds or feed additives.

In the invention, the active ingredient is, when used as a drug, administered in various dosage forms. Oral administration in the dosage forms such as tablets, capsules, granules, powders and syrups can be mentioned. These pharmaceutical preparations can be formulated in a usual manner by using, in an agent, known aids which can commonly be utilized in the field of the drug formulation technique, such as an excipient, a binder, a disintegrant, a lubricant, a corrigent, a solubilizing agent, a suspending agent and a coating agent. The use amount thereof varies with the symptoms, age, body weight, administration schedule and dosage form. It can be administered to an adult per day usually at a dose of from 0.01 ng to 1,000 mg per kg of weight in intravenous administration, at a dose of from 0.01 mg to 1,000 mg per kg of weight in intramuscular administration, and at a dose of from 0.05 to 10 g per kg of weight, preferably from 0.1 to 5 g per kg of weight in oral administration.

In the invention, DFA III is administered before delivery. However, it may be administered after delivery as required. For example, immediately after delivery and 6 hours after delivery and, as required, further 12 hours after delivery, DFA III may be administered in the range of from the foregoing dose per day to a dose which is twice the foregoing dose.

When DFA III is administered, vitamin D and, as required, calcium (preferably after delivery) may be jointly used. The doses of these are not particularly limited, Vitamin D is administered as vitamin $D_3$ at a dose of, usually from 0.5 to 7 μg, preferably from 1 to 4 μg, more preferably from 1.5 to 15 μg per day. Calcium is administered at a dose of from 50 to 500 mg, preferably from 200 to 450 mg, more preferably from 300 to 400 mg per day. Commercial products thereof are also available. Vitamin $D_3$ and calcium may be administered by adjusting the numbers of tablets thereof such that vitamin $D_3$ is 2.5 μg and calcium is 350 mg.

In case of a cow, vitamin D may be administered, as a tentative standard, at a dose of from 5,000 to 20,000 IU, preferably from 8,000 to 15,000 IU per day or for one administration. When calcium carbonate is used as calcium, it may be administered at a dose of from 50 to 200 g, preferably from 80 to 120 g for one administration.

Examples of vitamin D include vitamin $D_2$, vitamin $D_3$ and precursors thereof. It can be used for supplementing or enhancing the effect of accelerating calcium absorption of DFA.

The calcium agent refers to all agents which are permitted to be used in feeds or foods. Specific examples thereof include calcium gluconate, calcium propionate, calcium carbonate, calcium primary phosphate, calcium secondary phosphate, calcium tertiary phosphate, calcium chloride, oyster shell, powdered bones and the like, which are not critical, though. Vitamin D and/or calcium can jointly be used with DA not only for anticalcipenic activity but also for diuretic activity and antiedemic activity.

Advantage of the Invention

The invention brings forth the effects that the calcium concentration in blood of humans or animals is increased using agents for humans or animals or foods and drinks for humans or animals or feed compositions characterized by comprising DFA as an active ingredient to not only improve hypocalcemia in delivery but also improve lactation and decrease periparturient diseases. Further, since the active ingredient of the invention has the diuretic activity, it helps to maintain the health of humans or animals and to alleviate diseases such as udder edema.

The invention is quite characteristic in that the inhibition of the decrease in calcium concentration in blood after delivery has been successfully attained for the first time with quite a unique idea of administering DFA before delivery, not after delivery and in that it has been confirmed that the administration is more effective before delivery than after delivery. Therefore, according to the invention it is also possible to inhibit the decrease in calcium concentration in blood or maintain the calcium concentration in blood and further increase it.

Upon inhibiting the decrease in calcium concentration in blood, a pregnant woman whose calcium concentration is liable to decrease after delivery in particular can maintain the health and inhibit the decrease in amount of mother's milk and the decrease in composition of mother's milk.

Regarding the cow, the foregoing marked effects are brought forth, and also effects peculiar to the cow are also exhibited. That is, it has beer said that the decrease in calcium concentration in blood leads to ananastasia and decrease in appetite which influence many diseases in calving. However, supply of DFA III at a dry period eliminates the influence owing to aging, prevents the decrease in calcium concentration in blood, and quickens recovery to a normal condition. Accordingly, it makes a great contribution to the dairy farming field. Besides, according to the invention, life as the cow can be prolonged, which is economically quite profitable. In the dairy farming field, it has been recommended to limit calcium and phosphate in feeds at a dry period as a management for preventing hypocalcemia. However, it is quite difficult or substantially impossible to reduce the contents of calcium and phosphorus in feeds to the recommended ranges. According to the invention, there is no need to practice such a breeding control.

In addition, the invention is characteristic in that not mice or rats, but cows are used which are large in size and quite closer to pregnant women in lactation, and the data are highly reliable to humans. Needless to say, these data can directly be used for prevention and/or therapy of hypocalcemia of cows themselves, and the effects on other mammals can be estimated well from these data.

The invention is illustrated in more detail below by referring to Examples. However, the invention is not limited to Examples only.

EXAMPLE 1

In ruminants, for DFA III and DFA IV to accelerate calcium absorption, they have to reach intestines by avoiding degradation thereof in the rumen with microorganisms. Accordingly, degradability of DFA III and DFA IV in the rumen was examined.

A rumen liquid was collected from each of a rumen cannula-fitted Holstein steer to which 4 kg of a concentrate was supplied in consideration of controlling nutrition of a dry cow and which was caused to freely take hay and a cow in which a milk yield was 30 kg and a rate of a concentrate in a supplied feed was 55%. The liquid was filtered through a four-fold gauze to form an inoculum.

As a buffer, a 0.25 M phosphate buffer ($KH_2PO_4$ 6.8045 g+$Na_2HPO_4.12H_2O$ 26.8605 g/500 ml, pH 7.0) was used, and 1 g of DFA III or DFA IV per 100 ml of this buffer was added.

30 ml of the inoculum and 20 ml of the buffer were added to a 200-ml conical flask. After air inside the flask was replaced with carbon dioxide gas, the flask was closed with a rubber stopper fitted with a Bunsen valve, and the solution was cultured in an incubator of 39° C. In 0, 1, 2, 4, 8, 12 and 24 hours of the culturing, the culture solution was collected from the flask, and analyzed.

The culture solution in the flask was stirred. After 20 ml of the culture solution was collected, 0.1 ml of sulfosalicylic acid (20% solution was added for deproteinization. After centrifugation by 8,000 rotations for 10 minutes, the solution was filtered with a filter paper of 0.45 μm, and DFA III and DFA IV were analyzed by liquid chromatography.

Figure 1:
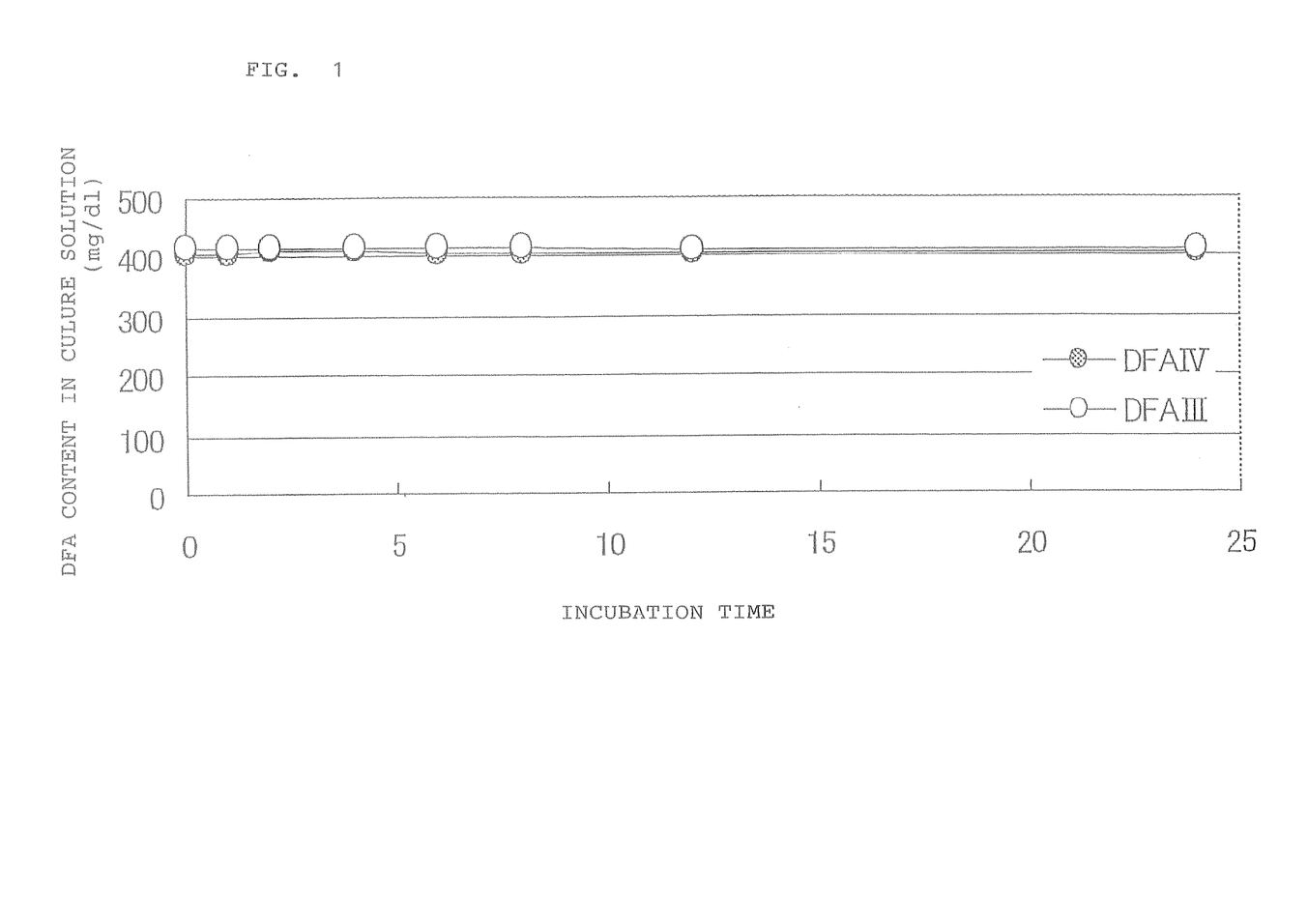
FIG. 1 shows a change in contents of DFA III and DFA IV by rumen incubation. However, regarding the change, no difference was found between the two culture solutions. Accordingly, an average value of the contents of the two culture solutions was used.

The amount of DFA III or DFA IV added to the culture solution was set at 400 mg/dl. Consequently, DFA III and DFA IV were not degraded in using any of the inoculums, and approximately the total amounts thereof were recovered in each incubation time (FIG. 1). It was confirmed that unless degraded by rumen microorganisms, DFA III and DFA IV reached the intestines in cows to accelerate absorption of calcium.

EXAMPLE 2

The effect of supply of DFA III and DFA IV on calcium metabolism, lactation and a urine excretion amount of cows was examined.

Nine Holstein cows (2 to 4 calvings, 90 to 120 days after calving, average body weight 642 kg, average milk yield 36 kg) were divided into three groups, and subjected to a test by 3×3 Latin squares with one period of 15 days (preliminary period of 10 days and main period of 5 days).

Regarding supplied feeds for a day, a grass silage, a cone silage and a beat pulp were used in fixed amounts of 3, 4 and 2 kg in terms of a dry weight respectively, and an amount of a concentrate (crude protein content 18% TDN content 74%) was ⅓ the milk yield. Further, a mineral agent and a vitamin agent were not supplied, and an insufficient feed for each cow was supplemented by supplying hay. These supplied feeds have the same contents in all cows, and they were caused to freely drink water.

The foregoing supply only was applied to a control group Supplied feeds and 100 g of DFA III were applied to a DFA III group, and supplied feeds and 100 g of DFA IV were applied to a DFA IV group.

The cows were accommodated in a metabolism test laboratory, and milking was conducted twice at 5 o'clock and 17 o'clock. The milk yield was measured and milk composition were analyzed for five days as the main period. The total amount of feces and urine was recovered for five days as the main period, and the fixed amounts thereof were mixed and subjected to analysis.

The results of the test were shown in Table 1. As is apparent from the results, no great difference was found among the groups in the dry matter intake and the calcium intake. The milk yield was increased in the DFA III and DFA IV groups by approximately 1 kg in comparison to the control group. No difference was found either among the groups in the milk fat rate and the milk protein rate. However, the calcium rate in milk was significantly increased in both of the DFA III and DFA IV groups in comparison to the control group (P<0.05). Regarding the excretion amount of calcium, the excretion amount in feces was significantly decreased (P<0.05) and the excretion amount in milk was significantly increased (P<0.05) in the DFA III and DFA IV groups. Although these results revealed that the digestible amount of calcium was increased by supplying DFA III and DFA IV, the effect for the storage amount thereof was not shown. No difference was observed in the amount of drunk water, whereas the urine amount was significantly increased in both of the DFA III and DFA IV groups (P<0.05). In the table, TDN indicates a total amount of a digestible nutrient.

From the foregoing, it has been confirmed that DFA III and DFA IV bring forth the excellent effect in calcium absorption of cows and also have the effect of increasing the calcium concentration in milk. The increase in urine amount has been also confirmed.

TABLE 1

Calcium metabolism and lactation
by supplying DFA III and DFA IV

|  | Control group | DFA III group | DFA IV group |
|---|---|---|---|
| Dry matter intake (kg/day) | 23.0 | 23.5 | 22.9 |
| Crude protein intake (kg/day) | 3.38 | 3.42 | 3.37 |
| TDN intake (kg/day) | 16.1 | 16.3 | 16.0 |
| Calcium intake (g/day) | 128 | 130 | 128 |
| Milk yield (kg/day) | 34.2 | 35.6 | 35.2 |
| Milk fat rate (%) | 3.87 | 3.86 | 3.92 |
| Milk protein rate (%) | 3.13 | 3.15 | 3.11 |
| Calcium rate in milk (mg/100 ml) | 105 | 121 | 118 |
| Excretion amount of calcium | | | |
| in feces (g/day) | 92.3 | 83.3 | 84.2 |
| in urine (g/day) | 2.3 | 4.2 | 4.0 |
| in milk (g/day) | 35.9 | 43.1 | 41.5 |
| Amount of calcium | | | |
| Digestible amount (g/day) | 35.7 | 46.7 | 41.8 |
| Storage amount (g/day) | −2.5 | −0.6 | −1.7 |
| Amount of drunk water (kg/day) | 113 | 114 | 110 |
| Urine amount (kg/day) | 15.3 | 20.8 | 20.0 |

EXAMPLE 3

The influence of DFA III and DFA IV on the calcium concentration in blood in calving of cows was examined.

As test cows, 15 Holstein calving cows with two or more calvings were used, and divided into three groups each consisting of 5 cows. Immediately after calving, the blood was sampled from the tail root. 300 ml of warm water was orally administered to the control group. 100 g of DFA III and 100 g of DFA IV each dissolved in 250 ml of warm water were orally administered to the DFA III group and the DFA IV group respectively. The blood was sampled from the tail root after 6 hours and 60 hours from the blood sampling immediately after calving. The degree of the udder edema was also confirmed by palpation.

Regarding the feeds supplied after calving, the cows were caused to freely take 20 kg/day of TMR containing a grass silage, a corn silage and a concentrate (hereinafter referred to as a mixed feed: forage rate 47.8%), 4 kg of a concentrate and hay. The contents of supplied feeds, the requirement and the difference rate are shown in Table 2 below. Conditions of calculating the requirement are as follow: day after calving—3, 2 calvings, body weight—612 kg, milk yield—20 kg, milk fat rate—4.0%, and milk protein rate—3.2%. NEl indicates a net energy of lactation, and efNDF indicates an effective neutral detergent insoluble fiber.

TABLE 2

Contents of supplied feeds, requirement and replenishment rate

|  | Supply amount kg | Dry matter % | NEI Mcal/kg | Crude protein DM % | efNDF DM % | Ca DM % | F DM % |
|---|---|---|---|---|---|---|---|
| TMR | 20.0 | 41.1 | 1.61 | 15.8 | 27.5 | 0.61 | 0.36 |
| Concentrate | 4.0 | 88.0 | 1.93 | 21.6 | 5.6 | 0.85 | 0.56 |
| Hay | 3.4 | 90.3 | 0.86 | 8.0 | 71.5 | 0.21 | 0.26 |
| Supply amount (kg, Mcal, g) |  | 14.8 | 22.7 | 2.3 | 4.7 | 87 | 57 |
| Requirement (kg, Mcal, g) |  | 14.8 | 25.0 | 2.2 | 3.6 | 98 | 63 |
| Difference rate (%) |  | 100 | 91 | 104 | 130 | 89 | 90 |

The blood was centrifuged at 3,000 rpm for 10 minutes, and the serum portion was stored at −30° C. until analysis. Calcium was analyzed by the OCPC method. The degree of udder was examined by palpation. A heavy degree was defined as 4, a medium degree as 3, a light degree as 2 and a normal degree as 1 respectively. The results were shown in Tables 3 and 4 respectively.

TABLE 3

Change in calcium concentration in blood by
oral administration of DFA III and DFA IV

| Time that lapses after first blood sampling | Calcium concentration in blood (mg/dl) | | |
|---|---|---|---|
|  | Control group | DFA III group | DFA IV group |
| 0 | 7.3 | 7.3 | 7.1 |
| 6 | 7.3 | 8.3 | 8.0 |
| 60 | 7.2 | 8.0 | 8.0 |

TABLE 4

Degree of udder edema by oral administration
of DFA III and DFA IV

| Time that lapses after first blood sampling | Degree of udder edema* | | |
|---|---|---|---|
|  | Control group | DFA III group | DFA IV group |
| 0 | 3.3 | 3.3 | 3.1 |
| 6 | 3.5 | 3.0 | 2.8 |
| 60 | 2.0 | 1.1 | 1.2 |

*A heavy degree was defined as 4, a medium degree as 3, a light degree as 2 and a normal degree as 1.

As is apparent from the foregoing results, the calcium concentration in blood immediately after calving was from 7.1 to 7.3 mg/dl in the respective groups. The calcium concentration in blood in 6 hours was not increased in the control group. Meanwhile in both of the DFA III group and the DFA IV group, the calcium concentrations in blood were increased by approximately 1 mg/dl from immediately after calving and reached 8.3 mg/dl and 8.0 mg/dl respectively. However, in 60 hours, the calcium concentration in blood became 8.0 mg/dl in the DFA III group, and a tendency of increase was not observed either in the DFA IV group from 6 hours. Incidentally, no cow having a milk fever symptom was observed in any of these groups. The degree of udder edema was increased in 6 hours in the control group. Meanwhile, it was improved in both of the DFA III group and the DFA IV area, and returned to nearly a normal degree in 60 hours.

From the foregoing results, it was confirmed that DFA III and DFA IV increased the calcium concentration in blood immediately after calving to reduce the udder edema.

EXAMPLE 4

The effect of DFA III and calcium and vitamin D on the calcium concentration in blood at the time of calving of cows was examined.

As test cows, 15 Holstein calving cows with 2 or more calvings were used, and divided into three groups each consisting of 5 cows. Immediately after calving, the blood was sampled from the tall root. 100 g of DFA III dissolved in 250 ml of warm water was orally administered to the DFA III group. DFA III and calcium carbonate in amounts of 100 g each which were dissolved in 200 ml of warm water were orally administered to the DFA III+Ca group. DFA III and calcium carbonate in amounts of 100 a each and 10,000 IU of vitamin D which were dissolved in 200 ml of warm water were orally administered to the DFA III+Ca+VD group. The blood was sampled from the tail root after 6, 24 and 70 hours from the blood sampling immediately after calving.

The supply of the feeds and the analyses of the calcium concentration in blood were conducted in the same manner as in Example 3. The results were shown in Table 5.

TABLE 5

Change in calcium concentration in blood by DFA III and calcium and vitamin D

| Time that lapses after first blood sampling | Calcium concentration in blood (mg/dl) | | |
|---|---|---|---|
| | DFA III group | DFA III + Ca group | DFA III + CA + VD group |
| 0 | 6.7 | 6.4 | 7.4 |
| 6 | 7.9 | 8.4 | 9.1 |
| 24 | 7.7 | 8.0 | 9.3 |
| 70 | 8.5 | 9.1 | 9.1 |

As is apparent from the foregoing results, the calcium concentration in blood immediately after calving was from 6.4 to 7.4 mg/dl, and the DFA III+Ca group showed the lowest value. In 6 hours, the calcium concentration in blood was increased in the DFA III group by 1.2 mg/dl, in the DFA III+Ca group by 2.0 mg/dl and in the DFA III+Ca+VD group by 1.7 mg/dl in comparison to that immediately after calving. In 24 hours, the calcium concentration in blood was lower in the DFA III group and the DFA III+Ca group than in 6 hours. However, the calcium concentration in blood was more increased in the DFA III+Ca+VD group, and reached 9.3 mg/dl considered to be a normal value. This concentration was maintained also in 70 hours. In 70 hours the calcium concentration in blood in the DFA III group and the DFA III+Ca group were 8.5 mg/dl and 9.1 mg/dl respectively, and the improvement in extent of recovery was observed in the DFA III+Ca group.

From the foregoing results, it was confirmed that the effect of DFA III was increased by the joint use of the calcium agent and more increased by the joint use of the calcium agent and vitamin D in comparison to the administration of DFA III alone.

EXAMPLE 5

The influence of the DFA III supply at a dry period on the calcium concentration in blood of cows after calving was tested in vivo using actual cows.

(1) Purpose

It has been so far considered that DFA III is administered to cows after caving which is effective for improving the calcium concentration in blood. On the other hand, the calcium concentration in blood is already decreased immediately after calving. As the decree of decrease is greater, vitality and appetite are weak and tend to be slowly recovered. Accordingly, DFA III was supplied at a dry period, and the influence of DFA III on the calcium concentration in blood immediately after calving was examined.

(2) Test groups

DFA III supply; DFA III (50 g/day) was supplied at a dry period from 3 weeks before an expected date of calving through calving.

Without DFA III supply; DFA III was not supplied before calving.

90 g of DFA III was, each time, supplied to both of the DFA III supply group and the group without DFA supply 0 hour and 6 hours after calving. At a dry period, 4 kg/day of a feed obtained by adding 12,000 IU of vitamin D to 4 kg of a feed was supplied to both the areas.

(3) Test Method

1) Test Cows

Cows with 2 or more calvings were used.

As DFA III supply cows, 10 cows which experienced calving after Apr. 30, 2004 were subjected to a test. As cows without DFA III supply, 38 cows which experienced calving from Jul. 14, 2002 through Apr. 18, 2004 and to which DFA III was not supplied at a dry period were used. Since the test started on Jul. 14, 2002, the test cows include 15 cows which experienced calving twice (8 DFA III supply cows and 7 cows without DFA III supply) during this period.

2) Supplied Feeds

In dry cows, milking was stopped 2 months before an expected date of calving. Then, a concentrate (crude protein content 18%, TDN 72%, Ca 0.9% P 0.5%) was supplied in an amount of 2 kg/day until 3 weeks before an expected date of calving. A concentrate (crude protein content 20%, TDN 75%, Ca 0.2%, P 0.5%) was supplied in an amount of 4 kg/day from 3 weeks before an expected date of calving through calving. As another feed, the cows were caused to freely take hay (crude protein content from 6 to 8%, TDN from 45 to 55%, Ca from 0.2 to 0.3%, P 0.2%) during the entire dry period. A mixture obtained by adding 50 g of DFA III to 4 kg of the concentrate given 3 weeks before an expected date of calving was supplied to the DFA III supply cows. As the feeds supplied after calving, the cows were caused to freely take 20 kg/day of TMR containing a grass silage a corn silage and a concentrate (crude feed rate 47.8%), 4 kg of a concentrate (crude protein content 18%, TDN 72%, Ca 0.9%, P 0.5%) and hay.

3) Blood Sampling after Calving and a Schedule of DFA III Administration

In all cows, the blood was sampled from the tail root immediately after calving. Further, the blood sampling was performed from the same tail root after 6 hours, 24 hours and 72 hours from the blood sampling immediately after confinement (0 hour). In 0 hour and 6 hours for blood sampling, 90 g of DFA III, 100 g of calcium carbonate and 10,000 IU of vitamin D dissolved in warm water were orally administered each time.

4) Method of Analyzing Calcium in Blood

The blood was centrifuged at 3,000 rpm for 10 minutes, and the serum portion was stored at −30° C. until analysis. The calcium concentration was measured by the OCPC method.

(Results)

Figure 2:
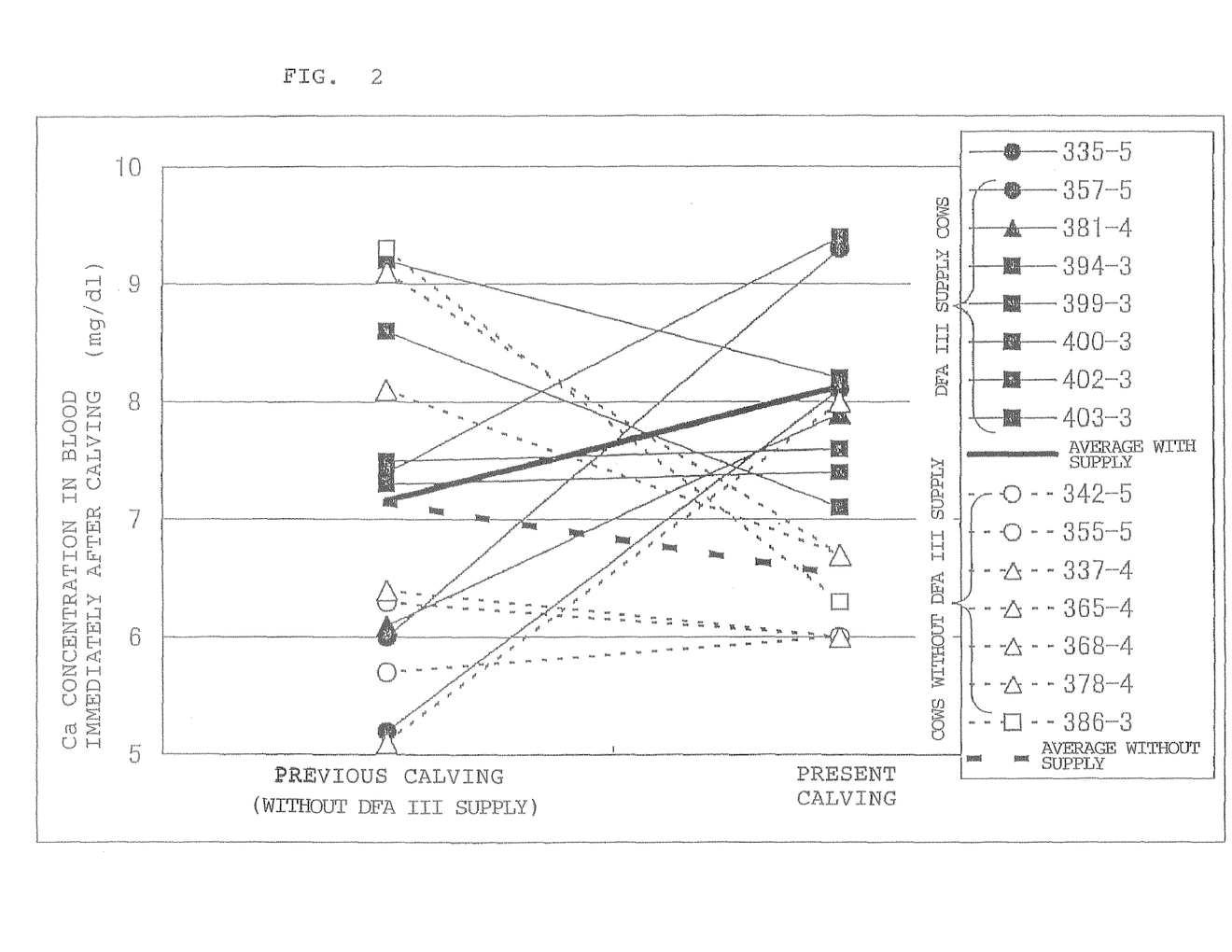
FIG. 2 shows influence of DFA III supply to the same cow at a dry period on the calcium concentration in blood immediately after calving. Before calving, DFA III is not supplied to all cows in the previous calving (cows which experience calving previously). DFA III is supplied to DFA III supply cows in the present calving (cows which experience present calving) from 20 days before calving (50 g per day). Values at the right end of FIG. 2 indicate the cow number and the parity of present calving (indicating number of calvings) which are hyphened.

1) Calcium Concentration in Blood Immediately after Calving of Cows which Experienced Calving Twice as Test Cows (Refer to FIG. 2)

DFA III is not supplied to the DFA III supply group and the group without DFA III supply at a dry period in the previous calving. The DFA III supply at a dry period was performed on only the DFA III supply cows in the present calving.

In the previous calving, the calcium concentrations in blood immediately after calving were or the average 7.2 mg/dl and 7.1 mg/dl in the DFA III supply cows and the cows without DFA III supply respectively and no difference was found between both the cows. In the present calving the calcium concentration in blood immediately after calving was 8.1 mg/dl in the DFA III supply cows, and was increased by 1.0 mg/dl in comparison to the previous calving. Meanwhile, it was 6.5 mg/dl in the cows without DFA III supply which was lower than in the previous calving by 0.6 mg/dl.

It is generally said that the calcium concentration in blood immediately after calving is decreased according to the aging. The cows without DFA III supply provided the results which proved this fact. However, the calcium concentration in blood was increased in the DFA III supply cows. Thus, it was considered that there was a high possibility of accelerating absorption of calcium from the intestines or accelerating migration of calcium from bones to the blood. Especially, in the present calving, there was no DFA III supply cow whose calcium concentration in blood was lower than 7 mg/dl in the present calving, and there was a tendency that a rate of increase was high in the aged cows. In the cows without DFA III supply except one cow, the calcium concentration in blood was lower than 7 mg/dl. Regarding the calcium concentration in blood immediately after calving of the present calving, a significant difference (p<0.01) was found between the DFA III supply cows and the cows without DFA III supply.

Figure 3:
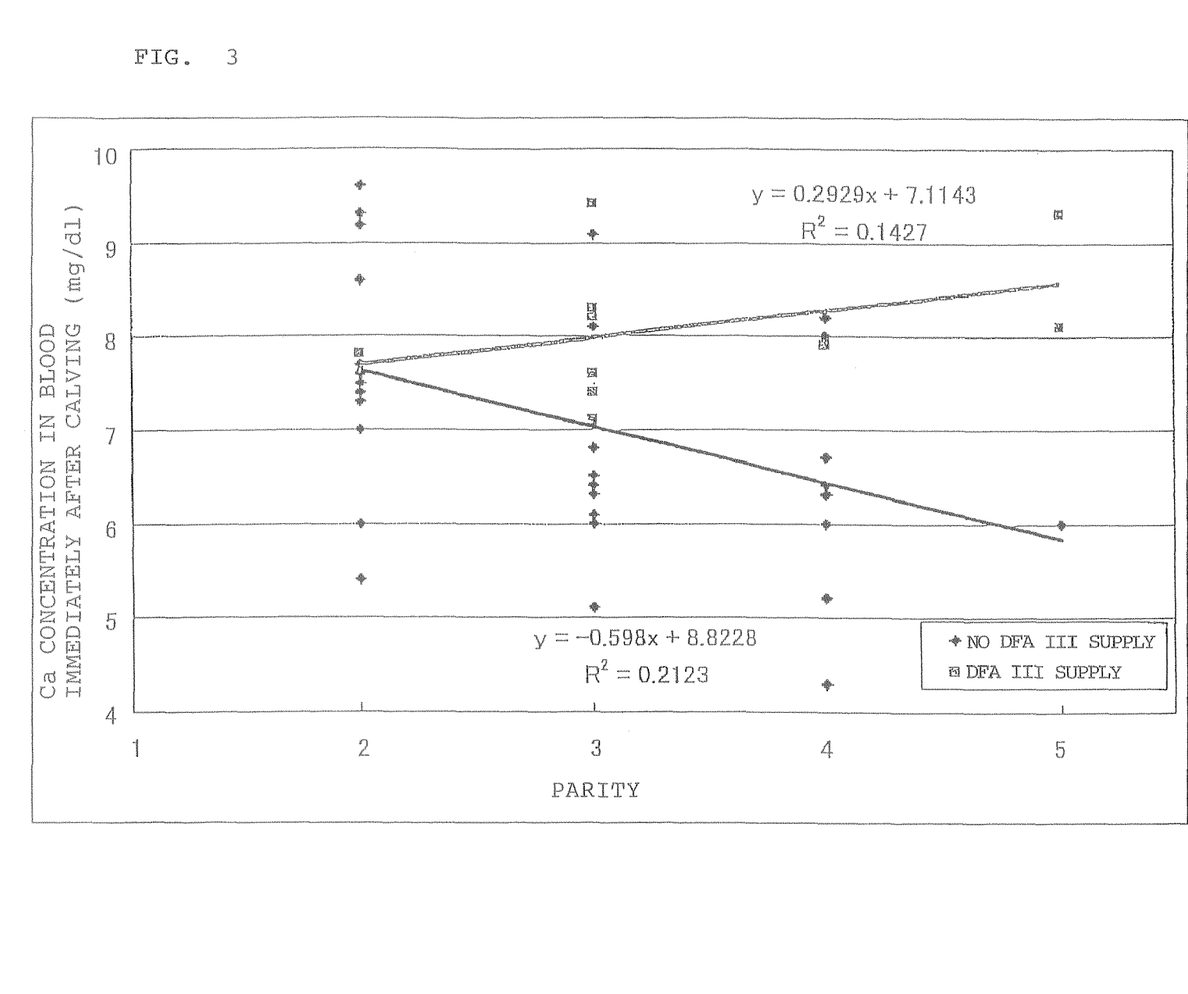
FIG. 3 shows an influence of DFA III supply at a dry period on a calcium concentration in blood immediately after calving (according to the parity).

2) Parity (Number of Calvings) and Calcium Concentration in Blood Immediately after Calving (Refer to FIG. 3)

FIG. 3 shows the calcium concentration in blood immediately after calving for each parity, and provides the data of all cows subjected to the test (10 DFA III supply cows and 38 cows without DFA III supply). In the cows without supplying DFA III at a dry period, the calcium concentration in blood was decreased as the parity was increased, and a relation of a calcium concentration in blood immediately after calving=−0.6×parity+8.8 was found (P<0.01). Meanwhile, in the DFA III supply cows, the calcium concentration in blood immediately after calving was not decreased by increasing the parity. In the regression formula of the DFA III supply cows, no significant difference is observed because of the small number of examples.

Figure 4:
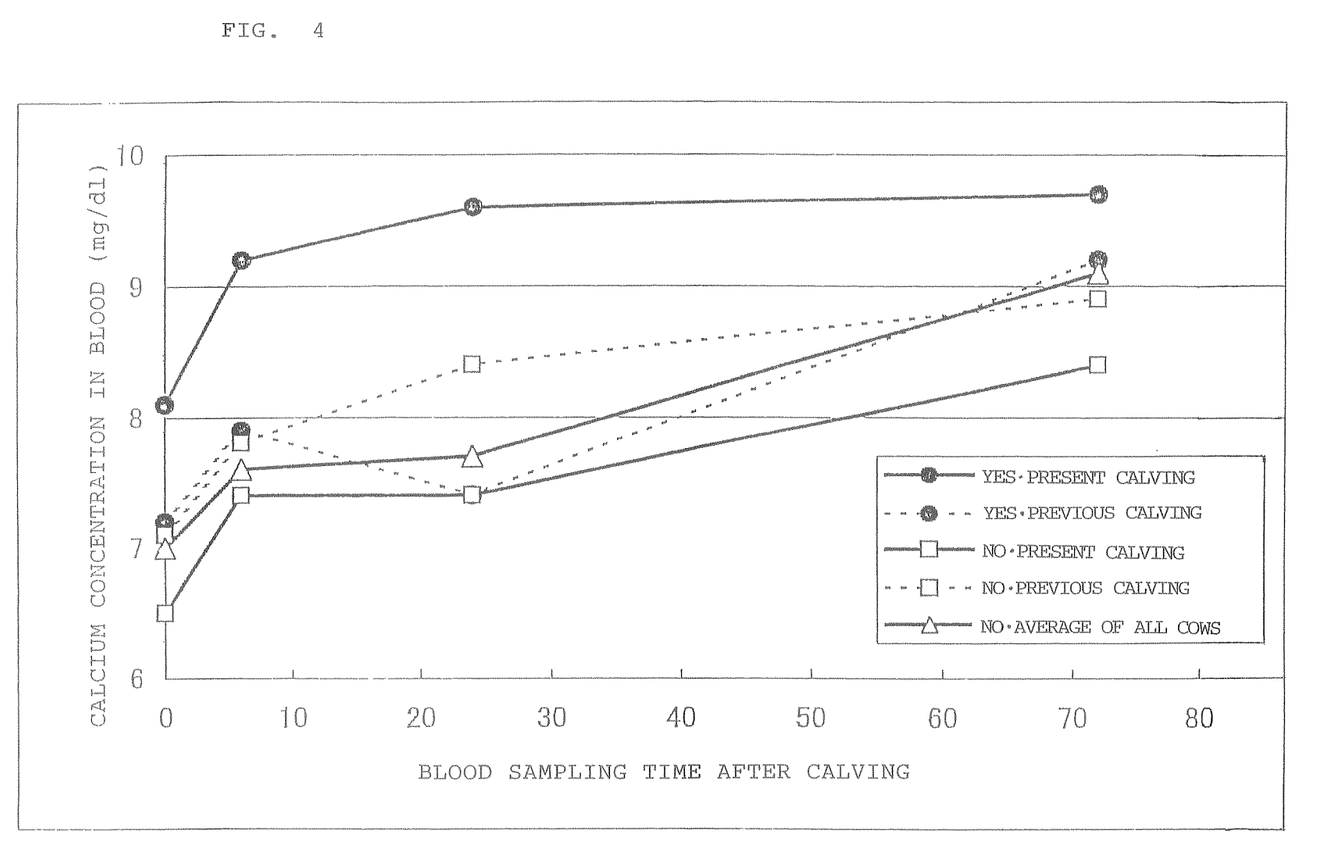

3) Change in Calcium Concentration in Blood after Calving (Refer to FIG. 4)

FIG. 4 shows the calcium concentration in blood with the lapse of time after calving. In remarks "Yes-Present calving" shows an average value of 8 cows to which DFA III was supplied at a dry period of the present calving. "Yes-Previous calving" shows data of the previous calving of "Yes-Present calving" cows. However, in the previous calving DFA III is not supplied at a dry period. "No-Present calving" shows an average value of 7 cows to which DFA III was not supplied at a dry period of the present calving. "No-Previous calving" shows data of the previous calving of "No-Present calving" cows, and DFA III is not supplied at a dry period. "No-Average of all cows" is an average value of all of 38 cows to which DFA III was not supplied at a dry period.

In "Yes-Previous calving" and "No-Previous calving", the calcium concentration in blood was shifted almost similarly except the calcium concentration in blood in 24 hours. Meanwhile, in "Yes-Present calving" the calcium concentration in blood was shifted at a higher level than in the previous calving, which was much different from the fact that the calcium concentration in blood in "No-Present calving" was shifted at a lower level than in the previous calving (a significant difference with P<0.01 was observed in 0, 6 and 24 hours). The normal value of the calcium concentration in blood is from 9 to 11 mg/dl. It is considered that when DFA III is supplied at a dry period the calcium concentration in blood reaches the normal value after approximately 6 hours. However, unless DFA III was supplied at a dry period, it took approximately 3 days for the calcium concentration in blood to be returned to the normal value. It was predicted that the more the calving was increased, the slower the recovery of the calcium concentration in blood became.

(5) Conclusion

As a result of the foregoing tests, the following matters have been confirmed.

1) When DFA III is supplied at a dry period, the calcium concentration in blood immediately after calving is more increased than in cows without supplying it. Consequently, ananastasia does not occur, the health of the cows are recovered quickly, and the milk yield is also increased.

2) It has been confirmed that when DFA III is supplied at a dry period, the calcium concentration in blood immediately after calving is not influenced by a decrease in calcium concentration owing to aging. As a result, a rate of cull and replacement has been reduced and life as a cow has been prolonged 3) It has been confirmed that unless DFA III is supplied at a dry period, the calcium concentration in blood immediately after parity is decreased as the calving is increased, and a decrease amount in one calving has been presumed to be 0.6 mg/dl.

4) When DFA III is supplied at a dry period, the calcium concentration in blood is quickly returned to a normal value, unlike cows without supply thereof which tend to be slowly returned to a normal value owing to aging.

5) The effect of increasing the calcium concentration in blood by supplying DFA III is greater at a dry period than immediately after calving.

It has been said that the decrease in calcium concentration in blood leads to ananastasia and decrease in appetite which influence many diseases in calving. The supply of DFA III at a dry period eliminates the influence owing to aging, prevents the decrease in calcium concentration in blood, and quickens recovery thereof to a normal condition. Accordingly, it has been proved that the supply of DFA III makes a great contribution to the dairy farming field.

The invention claimed is:

1. A method of reducing the decrease in calcium concentration in blood after delivery in a cow, which comprises administering difructose anhydride (DFA) orally and/or parenterally to a cow at a dose of from 50 to 200 g per day for one cow from 3 weeks before an expected date of delivery to actual delivery to a cow at a dry-up period.

2. The method of claim 1, further comprising administering calcium and/or vitamin D.

3. The method of claim 2, comprising administering calcium.

4. The method of claim 2, comprising administering vitamin D.

5. The method of claim 2, comprising administering vitamin D and calcium.

* * * * *